(12) United States Patent
Busiashvili (10) Patent No.: US 11,647,942 B1
(45) Date of Patent: May 16, 2023

(54) DEVICE FOR MONITORING AND TREATING BRADYARRHYTHMIA

(71) Applicant: Stat Capsule Inc., Glendale, CA (US)

(72) Inventor: Yuri Busiashvili, Los Angeles, CA (US)

(73) Assignee: Stat Capsule Inc., Glendale, CA (US)

( * ) Notice: Subject to any disclaimer, the term of this patent is extended or adjusted under 35 U.S.C. 154(b) by 0 days.

(21) Appl. No.: 17/935,306

(22) Filed: Sep. 26, 2022

Related U.S. Application Data (63) Continuation-in-part of application No. 17/655,900, filed on Mar. 22, 2022, now Pat. No. 11,471,657.

(51) Int. Cl.
| | |
|---|---|
| *A61B 5/363* | (2021.01) |
| *A61B 5/00* | (2006.01) |
| *G16H 20/10* | (2018.01) |

(52) U.S. Cl.
CPC ............ *A61B 5/363* (2021.01); *A61B 5/0022* (2013.01); *A61B 5/4839* (2013.01); *A61B 5/746* (2013.01); *G16H 20/10* (2018.01)

(58) Field of Classification Search
CPC .................. A61M 31/00; A61M 35/10; A61M 2205/3306; A61M 2205/186; A61B 5/02427; A61B 5/02438; A61F 9/0026; A61F 9/0008
See application file for complete search history.

(56) References Cited

U.S. PATENT DOCUMENTS

| | | | |
|---|---|---|---|
| 3,446,209 A | 5/1969 | Macha | |
| 3,976,072 A | 8/1976 | Walker | |
| 4,146,029 A | * 3/1979 | Ellinwood, Jr. | ... A61N 1/37211 607/9 |
| 4,173,971 A | * 11/1979 | Karz | ..... A61B 5/0006 600/524 |
| 4,573,982 A | 3/1986 | Forbes et al. | |
| 5,627,611 A | 5/1997 | Scheiner | |
| 7,784,936 B2 | 8/2010 | Stinson | |
| 8,770,743 B2 | 7/2014 | Tsubota et al. | |

(Continued)

FOREIGN PATENT DOCUMENTS

| | | | |
|---|---|---|---|
| CN | 203619766 U | 6/2014 | |
| CN | 104586382 A | * 5/2015 | ............... A61B 5/04 |

(Continued)

OTHER PUBLICATIONS

Panneton WM. Controlled bradycardia induced by nasal stimulation in the muskrat, Ondatra zibethicus. J Auton Nerv Syst. Jul. 1990;30(3):253-63. doi: 10.1016/0165-1838(90)90257-j. PMID: 2229892. (Year: 1990).*

*Primary Examiner* — Nilay J Shah
(74) *Attorney, Agent, or Firm* — Ralph D. Chabot (57) ABSTRACT

A device and method for monitoring a human heart rate to determine whether a bradyarrhythmia event has occurred and if so determined, an electrocardiogram (ECG) rhythm strip is begun to be generated on a continuous basis in real-time and wirelessly communicated to a third party such as the patient's treating physician. The method comprises a pair of sensors for detecting heart rate, each sensor in contact with a respective ear of the patient. If a bradyarrhythmia event is determined; applying an anticholinergic medication to the conjunctiva of at least one eye and releasing ammonia vapor for inhalation by the patient.

11 Claims, 5 Drawing Sheets

(56) References Cited

U.S. PATENT DOCUMENTS

| | | |
|---|---|---|
| 10,201,468 B2 | 2/2019 | Ahn |
| 10,624,781 B2 | 4/2020 | Ivri |
| 2004/0092548 A1* | 5/2004 | Embleton ............ A61F 9/0008 514/310 |
| 2004/0207803 A1 | 10/2004 | Paukovits |
| 2009/0182291 A1 | 7/2009 | Eilat |
| 2009/0247967 A1 | 10/2009 | Delli, Jr. |
| 2012/0179122 A1 | 7/2012 | Eilat et al. |
| 2012/0253159 A1* | 10/2012 | Medina ............ A61B 5/14552 600/340 |
| 2015/0018781 A1 | 1/2015 | Rinderknect et al. |
| 2015/0148774 A1* | 5/2015 | Yao .................... A61M 5/1723 604/504 |
| 2015/0370320 A1 | 12/2015 | Connor |
| 2016/0296168 A1 | 10/2016 | Abreu |
| 2016/0354240 A1 | 12/2016 | Chauhan et al. |
| 2017/0071550 A1 | 3/2017 | Newberry |
| 2017/0095153 A1* | 4/2017 | Bardy ................. A61B 5/7282 |
| 2017/0156927 A1 | 6/2017 | Richter et al. |
| 2020/0229973 A1 | 7/2020 | Tsubota |
| 2020/0391029 A1 | 12/2020 | Mullins et al. |

FOREIGN PATENT DOCUMENTS

| | | |
|---|---|---|
| CN | 210277470 U | 4/2020 |
| KR | 20170123736 A | 11/2017 |
| RU | 2412676 C1 | 2/2011 |

* cited by examiner

DEVICE FOR MONITORING AND TREATING BRADYARRHYTHMIA

FIELD OF THE INVENTION

The present invention relates to the field of heart treatment.

BACKGROUND

The human heart is "wired up" to allow the spark of an electric impulse to travel in the heart and cause electromechanical excitation. The impulse is generated in the natural pacemaker i.e. a group of nervous cells called sinus node, located in the right atrium. The impulse travels from the atria through the atrioventricular node (AVN) to ventricles to activate the sinus node causing mechanical contraction of the heart that results in blood circulation throughout the body. This mechanical contraction is interpreted as a pulse. Normally the pulse rate is above 50 beats per minute. For pathological conditions, the pulse rate may drop below 40 beats per minute.

Bradycardia less than 40 beats per minute and asystolic pauses longer than 3 seconds are treated successfully with a permanent pacemaker which, when surgically implanted, continuously monitors heart rhythm. When slow heart rhythm or asystole is detected, the pacemaker is activated and accelerates heart rhythm on demand. Millions of implanted permanent pacemakers prevent strokes, recurrent loss of consciousness, and cardiac arrest.

The reason is that indications for implantation of an electronic permanent pacemaker have to be documented; specifically, episodes of severe bradycardia or asystole. These spontaneous episodes may sometimes occur rarely and escape the monitoring devices, that are used to document presence of the dangerously slow heart rhythm.

There are external pacemakers/defibrillators available, but those are worn for life threatening tachyarrhythmias, to prevent cardiac arrest as opposed to bradycardic cardiac arrest.

There are two components of the autonomic nervous system that control the heart rate: A) cholinergic, largely represented by vagal nerve; it slows down the heart rate and atrioventricular conduction; and, B) adrenergic, that stimulates heart rate and improves atrioventricular conduction. Both systems are normally in balance. During the day, the adrenergic autonomous nervous system prevails during the time of activity; and, vagal nerves dominate the body physiology while the body is at rest, typically during the night.

With age or in certain pathological conditions, such as sick sinus syndrome or conduction abnormalities in the heart, severe bradycardia and episodes of prolonged asystolic pause may occasionally occur and go unnoticed or result in life threatening complications before any preventive measures can be applied.

For the last decade transfemoral aortic valve replacement (TAVR) has become very popular because of it's success with elderly patients having severe aortic stenosis. An aortic valve prosthesis is implanted via the femoral arterial approach and the patient is usually discharged from the hospital within 48 hours. The aortic valve ring is very close to the hearts electrical conduction system, in particular, the atrioventricular node, which is routinely traumatized by prosthetic valve carrying balloon during its inflation at the time of valve deployment. As a result, it's a common location for development of an advanced heart block after valve deployment. Roughly 10% of all patients undergoing TAVR require permanent pacemaker implantation to prevent episodes of complete heart block. However, with many other patients being discharged from the hospital within 48 hours, episodes of transient heart block may occur days or weeks later, during the 2-3 month healing process.

As a result of a TAVR procedure, the surrounding tissues are injured and the healing period can takes weeks for the inflammation and trauma resulting from the stent placement to subside, just as for other myocardial injuries. In some patients, TAVR will cause the formation of scar tissue which can alter the normal electronic impulse or atrio-ventricular conduction and lead to atrioventricular conduction delay, or high degree atrioventricular block. The extreme expression of heart block is complete heart block (CHB).

In CHB, an electric impulse is not conducted to the pumping chamber ventricles, and the heart ceases to contract, which is a condition called cardiac standstill. A cardiac standstill lasting longer than 15 seconds is considered cardiac arrest.

There is no wearable medical device that is able to continually monitor heart rate, detect life threatening bradycardia and/or asystole, alert the user of its onset and automatically immediately discharge non electronic therapy on demand.

Some wearable heart rate monitors use photoplethysmography (PPG) sensors to measure heart rate. PPG sensors are typically worn on the wristband for convenience, but can be applied to the skin of the earlobe as well for heart rate monitoring.

It is well known sinus bradycardia or sudden onset of atrioventricular block can be treated with either intravenous administration of Atropine—an anticholinergic, or an adrenaline like sympathomimetic substance. Since discharged patients do not have access to intravenous delivered medication, the fastest way to increase the endogenous adrenaline production is by inhaling ammonia vapor which works through the olfactory reflex within seconds after inhalation. The need exists to monitor patients having sick sinus syndrome, especially at night to detect and prevent life-threatening bradycardia.

Some percentage of the patients experience syncope, collapse or die with sudden development of a high degree atrioventricular block progressing to CHB. Atropine intramuscularly or intravenously is used in a hospital setting to improve atrioventricular conduction.

Atropine has also been used for dilation of a pupil during an eye exam. Some of the Atropine applied to the eye is absorbed to the general blood circulation.

A need exists for monitoring of discharged patients following a TAVR procedure for onset of CHB and should such a condition arise, provide medication to treat the condition.

SUMMARY OF THE INVENTION

Described herein is a device and method to monitor a patient for a bradyarrhythmia event and if required, deliver one or more medications to the patient. More specifically, an anticholinergic medication such as Atropine is administered to the conjunctiva; and release of an inhalant that causes the body to release Adrenaline via an olfactory unconditional reflex.

This invention is designed to treat episodes of asystolic arrest which can follow the transition of the rhythm from rapid atrial fibrillation to sinus bradycardia and/or suddenly developed high degree atrioventricular block, especially in the first few weeks following a TAVR procedure.

Specifically, TAVR related blockage can occur within seconds, causing the patient to pass out or progress to cardiac arrest. For patients that are susceptible to this condition, it is vital that life-saving medication be immediately available.

Therefore, the invention is directed to monitoring for a bradyarrhythmia event and should that event occur, an anticholinergic medication such as Atropine will be administered to the conjunctiva area of the eye. Administration of the anticholinergic medication should occur within a short period of time, such as within ten seconds of the bradyarrhythmia event. Optionally, the device can further include an inhalant such as ammonia vapor, which when inhaled causes the body to release Adrenaline via an olfactory unconditional reflex. The combination of inhalant with the administration of an anticholinergic medication to the conjunctiva area of the eye, increases the chance for a patient to survive a bradyarrhythmia event outside of a hospital setting.

As defined herein, the term bradyarrhythmia event means either: 1) heart rate below 40 beats per minute; or, b) no heart beat for at least 3 seconds.

The device comprises a pair of sensors which detects heart rate which can be used for the generation of an electrocardiogram (ECG) rhythm strip and to thereafter administer medication. In a preferred embodiment, the device utilizes an eyeglass frame designed to automatically administer anticholinergic medication to the conjunctiva area of the eye and can further be designed for release of ammonia vapor automatically or manually for inhalation in response to a bradyarrhythmia event determination. Administration of the medications increase the chance of a patient surviving an asystolic event outside of a hospital setting; particularly when the patient is asleep.

If a bradyarrhythmia event is determined, the heart rate data obtained from the sensors is converted into ECG rhythm strip data either in a processing unit which is part of a module on the eyeglass frame or, more preferably, the heart rate data is transmitted to a separate handheld unit. The heart rate data, for example, can be transmitted first to a handheld unit such as a smartphone, smartwatch or other portable electronic unit wherein using an algorithm as part of an app, the heart rate data can be interpreted into ECG rhythm strip data that is displayed on the handheld unit and/or wirelessly communicated to the desired third party such as a treating physician or other medical staff. By way of example, in the case of the use of wireless sensors, the information detected by the sensors can be transmitted directly to the handheld unit for processing. Alternatively, the eyeglass frame can be designed with a module adapted to receive the information from the wired or wireless sensors, interpret the information into ECG rhythm strip data and thereafter communicate the data to the handheld unit for display and wireless communication to the desired third party. Thus, the processing of information and the determination of whether the patient is experiencing a bradyarrhythmia event could be handled by either a module attached to the frame or by an app on a handheld unit. Most preferably, the ECG rhythm strip data would only be wirelessly delivered to a third party upon the patient experiencing a bradyarrhythmia event based on the heart rate data received from the sensors and determined by either the eyeglass frame device or an app downloaded onto a handheld unit.

The device is operatively connected to a pair of sensors which are capable of acting as ECG electrodes, preferably PPG sensors that are attached to the earlobes of the patient. The sensors can be connected either wired or wireless. Alternatively, the sensors can be provided in the form of wired or wireless earbuds for positioning in the ear canal rather than to the lobes. The device further comprises a reservoir containing an anticholinergic medication and a means for delivery of the medication to the conjunctiva area of the eye. In one embodiment an ammonia inhalant capsule is attached to the eyeglass frame within a compartment designed to release the vapor from the capsule in response to the patient experiencing a bradyarrhythmia event. Optionally, the eyeglass frame device can include vibration and/or audible alerts for the patient.

In the event of a bradyarrthymia event, if the information is processed on the handheld unit, the unit would transmit a command to the module on the frame for release of medicament.

Wireless communication of the ECG rhythm strip data to a third party responsible for monitoring the patient's condition such as a physician or medical staff will decide, whether the reported rhythm strip constitutes an indication for an immediate hospital visit and permanent pacemaker implantation.

Following the recognition of a bradyarrhythmia event from information received from the sensors, Atropine is applied to the conjunctiva of at least one eye; either as eye drops or as a mist.

In another embodiment, to potentiate the antibradycardia effect of Atropine, an ammonia inhalant capsule is mounted to the eyeglass frame which can be manually crushed.

Since the recommended time required for healing of the tissue around the aortic valve prosthesis can be as long as 10-11 weeks post TAVR procedure, the use of the device should be for the same period of time.

The device includes a medication reservoir that can be integrated with the eyeglass frame or can be operatively connected thereto. The medication, for example, could be a 0.1% Atropine solution released as a drip or mist and the reservoir would contain about 1 cc of 0.1% Atropine.

Atropine delivered onto the conjunctiva is almost immediately absorbed and will increase heart rate, and temporarily reverse profound bradycardia. The timely administration of medication can prevent progression of severe bradycardia to asystole or higher degree atrioventricular block from occurring.

One method according to the invention for monitoring a patient's heart rate and dispensing a medication onto the conjunctiva of at least one eye in response to a bradyarrhythmia event comprises the steps of:

monitoring the patient's heart rate using a pair of sensors, each sensor in contact with a respective ear of the patient to determine the occurrence of a bradyarrhythmia event; and, if a bradyarrhythmia event has occurred, a) generating a real-time ECG rhythm strip and wirelessly communicating to a third party on a continuous basis for a period of time; and, b) dispensing an anticholinergic medication to the patient. The rhythm strip would begin to be generated after the app determines a bradyarrhythmia event has occurred. The data for the ECG rhythm strip would be received from the sensors in real-time and on a continuous basis. The rhythm strip would be generated for a period of time sufficient for a third party to render a determination. It is not likely that the period of time would exceed 30 minutes.

DETAILED DESCRIPTION OF THE PREFERRED EMBODIMENT

The figures presented herein are for illustrative purposes and the illustrated parts are not necessarily shown in correct proportion or scale.

The device and methodology described herein is specifically directed to patients who have undergone a TAVR procedure and have been discharged from the hospital. For these patients, the risk of experiencing a bradyarrhythmia event within weeks of hospital discharge is high.

The release of ammonia vapor can be before, concurrently or subsequent to administration of the anticholinergic medication.

Figure 1:
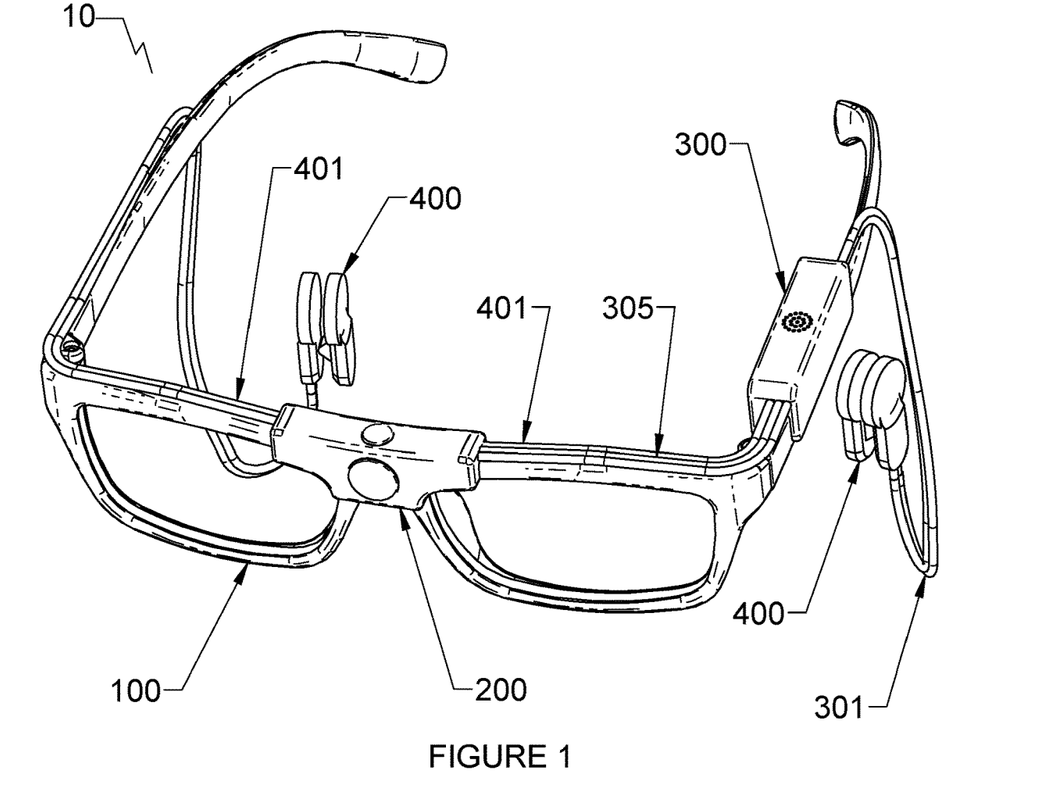
FIG. 1 is a perspective view of one embodiment of the device.

The methodology can be implemented by device 10 illustrated in FIG. 1 that is wirelessly linked to a smartphone or similar device (not shown). Device 10 comprises an eyeglass frame 100 having a sprayer 200 and a module 300.

Figure 3:
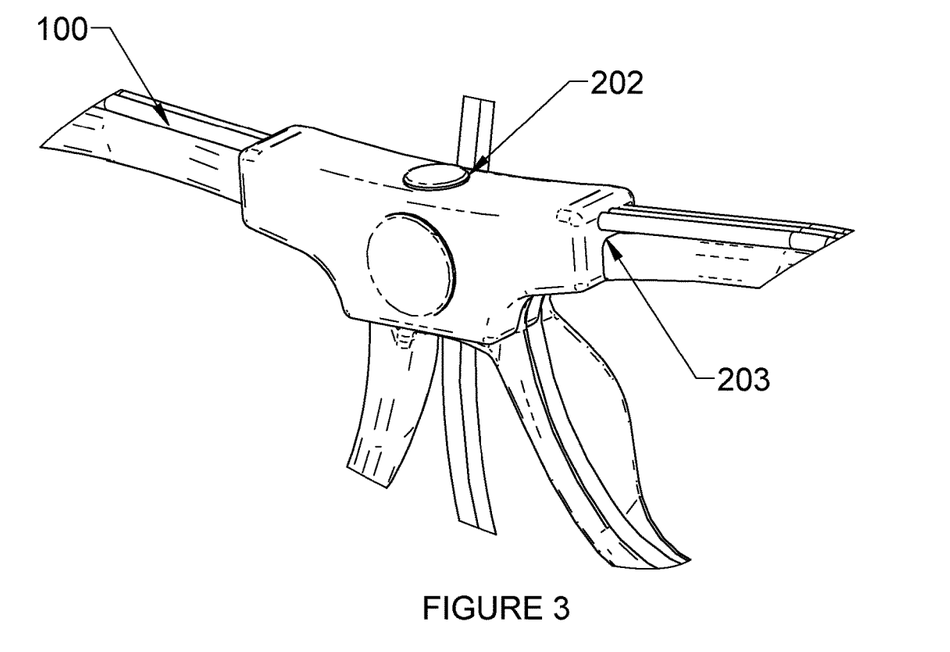
FIG. 3 is a close up view of the bridge portion of the device illustrated in FIG. 1.
Figure 4:
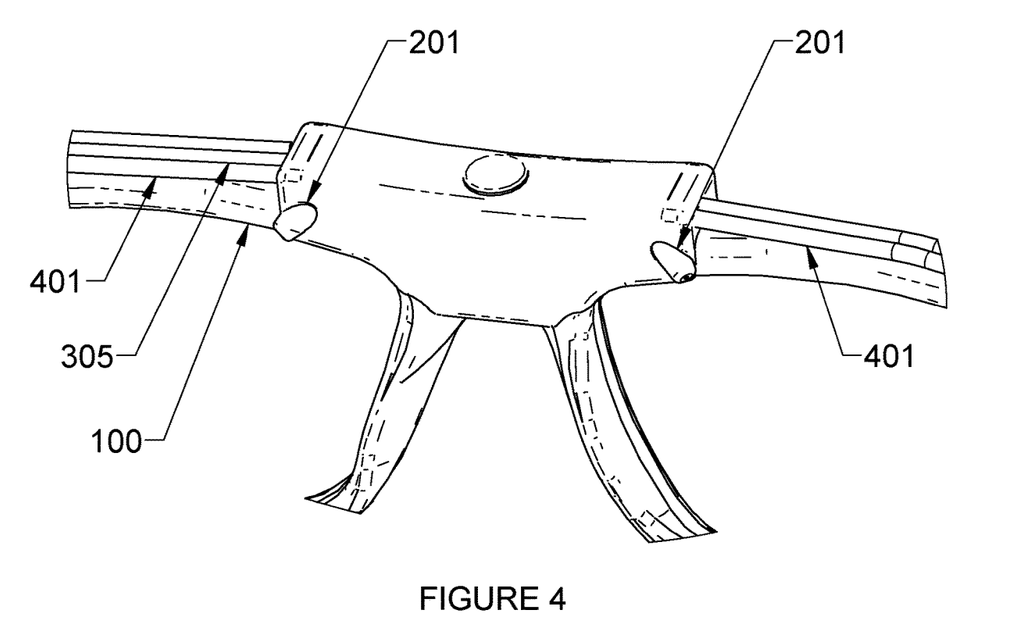
FIG. 4 is an alternate close up view of the bridge portion of the device illustrated in FIG. 1.

Sprayer 200 includes a reservoir (not shown) for storage of an anticholinergic medication such as Atropine. As best illustrated in FIG. 3, sprayer 200 includes a removable cap 202 for refilling the reservoir and a snap-on recess 203. Sprayer 200 can be designed to fit on the bridge of eyeglass frame 100 with recess 203 ensuring a secure attachment. Sprayer 200 includes a pair of nozzles 201 as best shown in FIG. 4. These nozzles discharge the medication from sprayer 200 to the conjunctiva of the patient.

Figure 2:
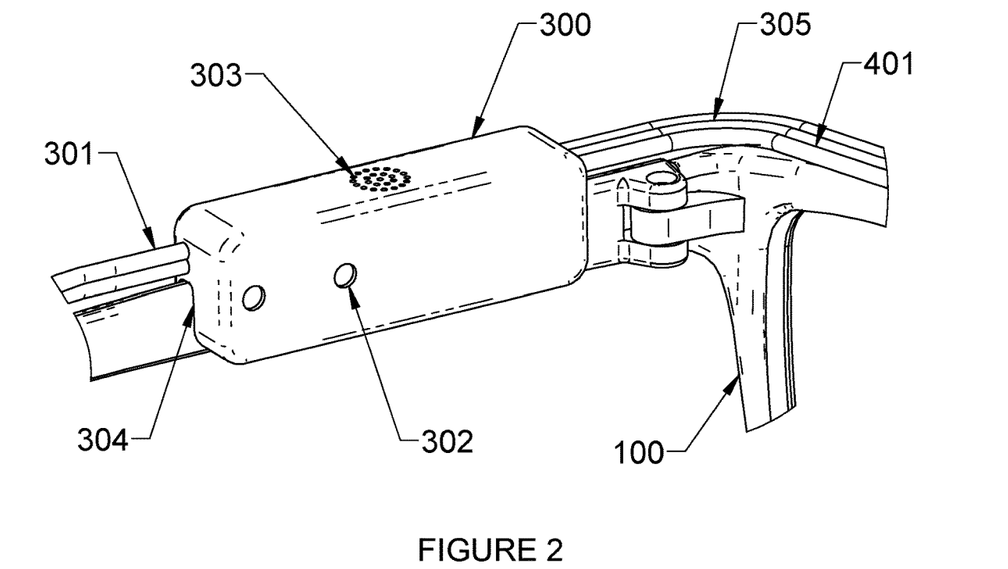
FIG. 2 is a close up view of the module illustrated in FIG. 1.

Module 300 is best illustrated in FIG. 2 and comprises wires 301 and 401 for operative connection to respective PPG sensors 400. Wire 305 operably connects module 300 to sprayer 200. Module 300 further comprises a charging terminal 302 for charging an internal battery (not shown), an audio speaker and a vibration unit (not shown), a transmitter/receiver (not shown) for wireless communication of information detected by sensors 400 to a hand held unit or smartphone (not shown). Module 300 further includes a snap-on recess 304 to securely attach Module 300 to eyeglass frame 100.

Figure 5:
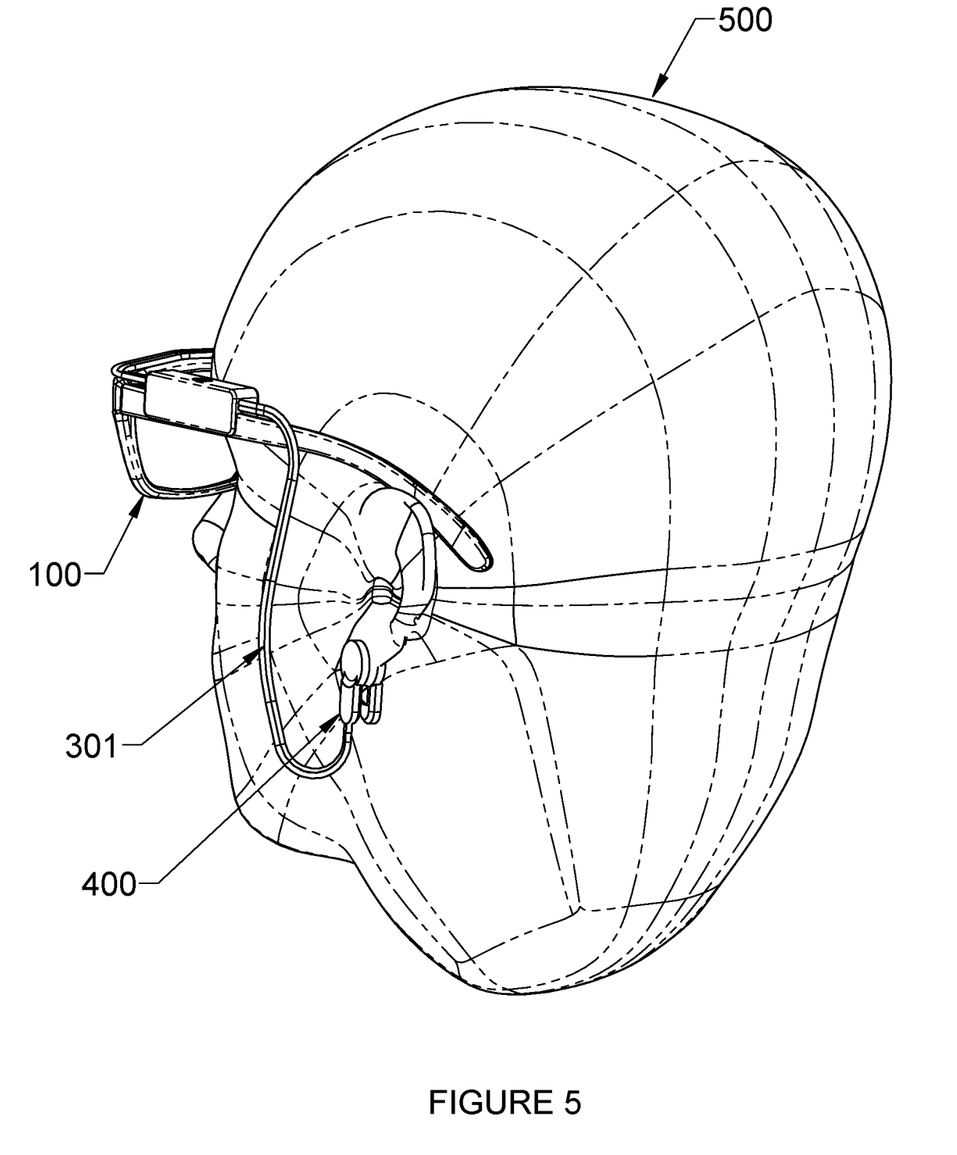
FIG. 5 is a view of a sensor wired to the module and attached to an earlobe of a patient.

In order for device 10 to be worn while the patient sleeps, a band (not shown) connected on either end to respective temples of frame 100 is used to maintain the positioning of device 10 to the patient's head. PPG sensors 400 contact respective earlobes of a patient shown as part of human head 500 in FIG. 5.

Figure 6:
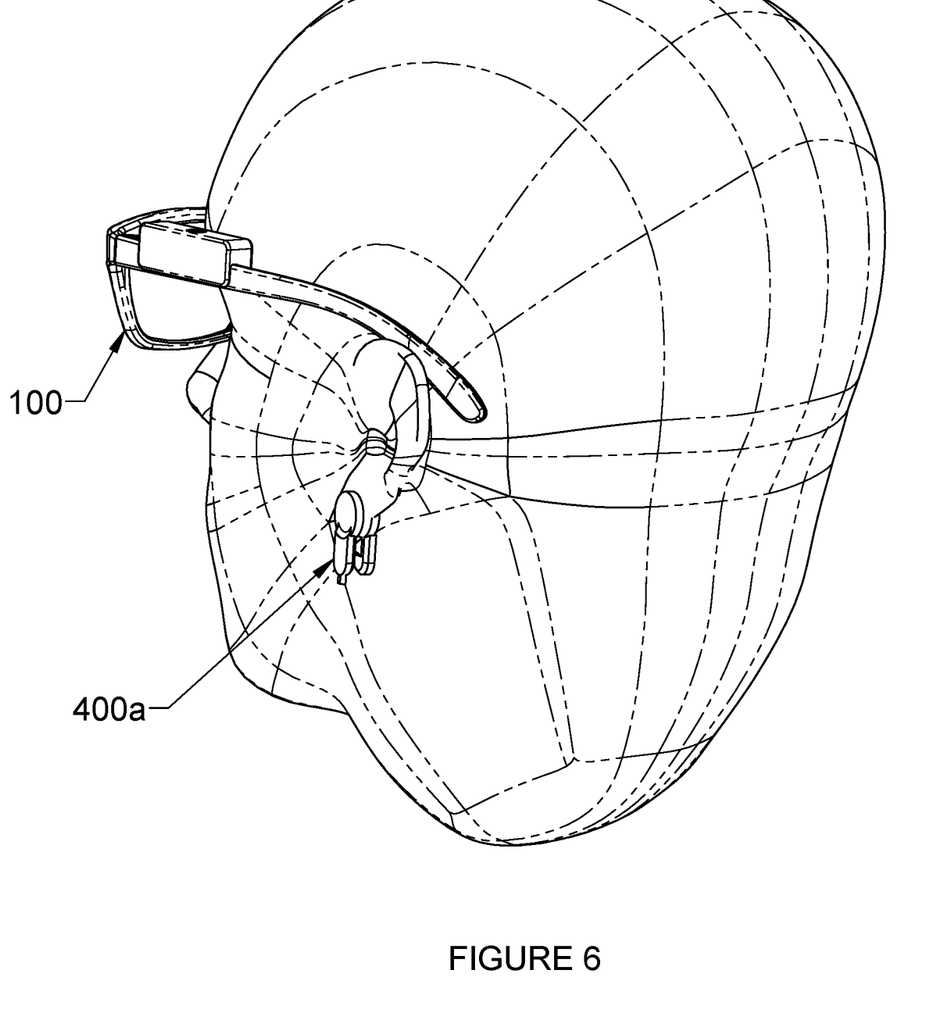
FIG. 6 is an alternate embodiment in which a wireless sensor is attached to an earlobe of a patient.

In an alternative embodiment, wired PPG sensors 400, and wires 301, 401 are replaced with wireless sensors 400a as illustrated in FIG. 6.

Figure 7:
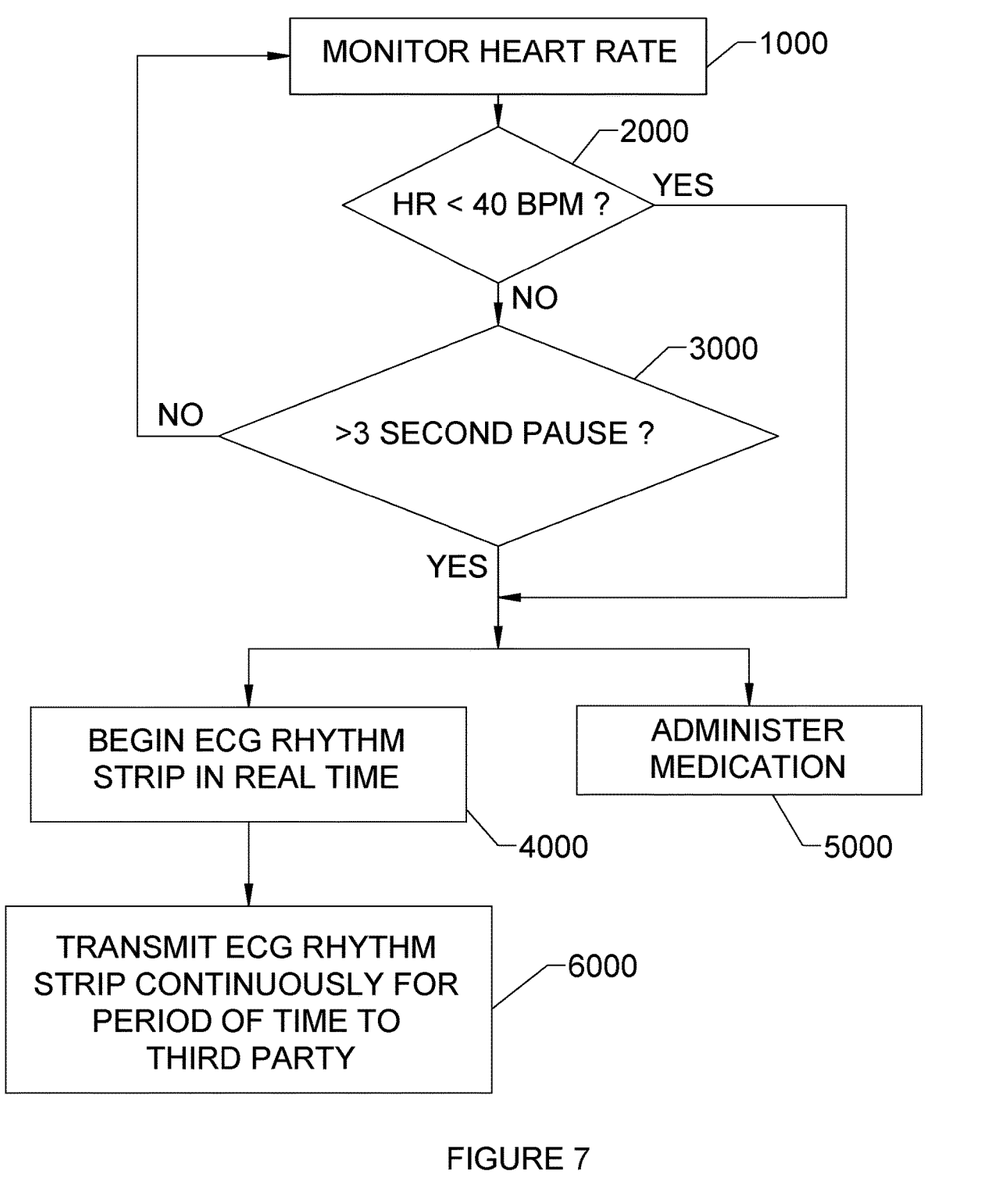
FIG. 7 is a flowchart illustrating the method of the invention.

One example of use of the method is using wireless sensors 400a utilized for communication with a smartphone. FIG. 7 is a flowchart indicating the methodology. A patient will have his heart rate monitored 1000 by wireless sensors 400a wirelessly transmitted to an app on the smartphone. The app will determine if the monitored heart rate is below 40 beats per minute 2000. If no, the app will next determine if at least a three second pause was measured between consecutive heart beats 3000. If no, the process returns to monitoring heart rate step 1000. If yes to either step 2000 or 3000, a bradyarrhythmia event will be determined to have occurred and the app will begin to generate an ECG rhythm strip in real-time 4000 and transmit a signal to module 300 to administer medication 5000. Module 300 would activate sprayer 200 to release the anticholinergic medication thru nozzles 201 within 10 seconds as well as the release of ammonia vapor from ports 303 of module 300. The smartphone will wirelessly transmit the ECG rhythm strip on a continuous basis for a period of time to a third party such as the patient's treating physician or other medical staff 6000. The period of time would be a sufficient length of time for the third party to evaluate the data transmitted. Module 300 is also equipped with a speaker and vibration device (not shown) for alerting the patient, particularly if asleep.

I claim:

1. A method for monitoring a patient's heart rate and dispensing an anticholinergic medication onto the conjunctiva of at least one eye in response to a bradyarrhythmia event comprising the steps of:
    monitoring the patient's heart rate using a pair of sensors, each sensor in contact with a respective ear of the patient to determine an occurrence of the bradyarrhythmia event; the pair of sensors in operative contact with a medication dispenser for delivery of the anticholinergic medication to the conjunctiva of the at least one eye and,
    if a bradyarrhythmia event has occurred, dispensing the anticholinergic medication to the patient.

2. The method of claim 1 further comprising the step of generating a real-time ECG rhythm strip and wirelessly communicating to a third party on a continuous basis.

3. The method of claim 1 in which an ECG rhythm strip is wirelessly communicated first to a smartphone that thereafter wirelessly communicates the ECG rhythm strip to a third party.

4. The method of claim 1 further comprising the step of releasing ammonia vapor after the bradyarrhythmia event.

5. The method of claim 4 further comprising the step of generating a real-time ECG rhythm strip and wirelessly communicating to a third party on a continuous basis.

6. A device for monitoring a patient's heart rate and dispensing the medication onto the conjunctiva of at least one eye comprising:
    an eyeglass frame having a bridge;
    a pair of sensors;
    a module connected to the eyeglass frame comprising: an input for operable connections to each sensor; an ammonia inhalant; an alert mechanism selected from the group consisting of audible, vibration or both; and, a transmitter for wireless communication; and,
    a spray mechanism attached upon the bridge of the frame having a reservoir for containing a predetermined amount of the anticholinergic medication; the spray mechanism having at least one nozzle for discharging the anticholinergic medication.

7. The device of claim 6 wherein the anticholinergic medication is Atropine.

8. The device of claim 6 further comprising wires for operable connection of the sensors to the module.

9. The device of claim 6 wherein the transmitter is for communication with a handheld unit.

10. A method for monitoring a patient's heart rate and dispensing a medication onto the conjunctiva of at least one eye in response to a bradyarrhythmia event comprising the steps of:

monitoring the patient's heart rate to determine an occurrence of the bradyarrhythmia event; and, if a bradyarrhythmia event has occurred, generating a real-time ECG rhythm strip and thereafter, wirelessly communicating to a third party on a continuous basis during which dispensing the medication onto the conjunctiva of the at least one eye.

11. The method of claim 10 further comprising the step of releasing ammonia vapor.

\* \* \* \* \*